United States Patent
Kolb et al.

(10) Patent No.: US 10,046,121 B2
(45) Date of Patent: Aug. 14, 2018

(54) INHALATION DEVICE WITH FEEDBACK SYSTEM

(71) Applicant: VECTURA GMBH, Gauting (DE)

(72) Inventors: Tobias Kolb, Neuried (DE); Tobias Hoffman, Gilching (DE); Sebastian Schwendner, Olching (DE); Martin Huber, Furstenfeldbruck (DE); Bernhard Muellinger, Munich (DE)

(73) Assignee: VECTURA GMBH, Gemuenden (DE)

( * ) Notice: Subject to any disclaimer, the term of this patent is extended or adjusted under 35 U.S.C. 154(b) by 665 days.

(21) Appl. No.: 14/368,730

(22) PCT Filed: Dec. 27, 2012

(86) PCT No.: PCT/EP2012/076963
§ 371 (c)(1),
(2) Date: Jun. 25, 2014

(87) PCT Pub. No.: WO2013/098334
PCT Pub. Date: Jul. 4, 2013

(65) Prior Publication Data
US 2014/0352690 A1    Dec. 4, 2014

(30) Foreign Application Priority Data

Dec. 27, 2011 (EP) ................................. 11195773
Oct. 26, 2012 (EP) ................................. 12190139

(51) Int. Cl.
*A61M 11/00* (2006.01)
*A61M 15/00* (2006.01)
*A61M 16/00* (2006.01)

(52) U.S. Cl.
CPC ........... *A61M 11/005* (2013.01); *A61M 11/00* (2013.01); *A61M 15/002* (2014.02);
(Continued)

(58) Field of Classification Search
CPC .................... A61M 111/005; A61M 11/00; A61M 15/002; A61M 15/0085; A61M 2205/18;
(Continued)

(56) References Cited

U.S. PATENT DOCUMENTS 5,794,612 A * 8/1998 Wachter ............ A61M 15/0086
128/200.23
5,906,202 A * 5/1999 Schuster ........... A61M 15/0045
128/203.12
(Continued)

FOREIGN PATENT DOCUMENTS

EP          2283887      2/2011
WO       1992011808      7/1992
(Continued)

OTHER PUBLICATIONS

Written Opinion of the International Searching Authority, PCT/EP2012/076963.

*Primary Examiner* — Gregory Anderson
*Assistant Examiner* — Margaret Luarca
(74) *Attorney, Agent, or Firm* — Matthew S. Gibson; Ryan P. Cox; Reed Smith LLP

(57) ABSTRACT

The invention provides an inhalation device for enabling a user to inhale at a desired inspiratory flow rate and/or pressure, comprising a feedback system configured to indicate to a user by means of a signal during an inhalation maneuver whether an inhalation parameter, such as the inspiratory flow rate, is within a predefined target range. The signal may be an optical or a non-optical signal, such as a light signal, an acoustic signal, or a tactile signal.

12 Claims, 5 Drawing Sheets

(52) U.S. Cl.
CPC . *A61M 15/0085* (2013.01); *A61M 2016/0027* (2013.01); *A61M 2016/0039* (2013.01); *A61M 2205/18* (2013.01); *A61M 2205/3303* (2013.01); *A61M 2205/3368* (2013.01); *A61M 2205/3375* (2013.01); *A61M 2205/43* (2013.01); *A61M 2205/44* (2013.01); *A61M 2205/581* (2013.01); *A61M 2205/582* (2013.01); *A61M 2205/584* (2013.01)

(58) Field of Classification Search
CPC ........ A61M 2205/581; A61M 2205/43; A61M 2205/584; A61M 2205/44; A61M 2205/582
See application file for complete search history.

(56) References Cited

U.S. PATENT DOCUMENTS

| | | | |
|---|---|---|---|
| 6,358,058 B1 * | 3/2002 | Strupat | A61B 5/0876 434/262 |
| 7,448,375 B2 | 11/2008 | Gonda et al. | |
| 2004/0187869 A1 * | 9/2004 | Bjorndal | A61B 5/087 128/203.15 |
| 2005/0087189 A1 | 4/2005 | Crockford | |
| 2006/0060199 A1 * | 3/2006 | Lampotang | A61M 16/0078 128/205.13 |
| 2011/0030682 A1 * | 2/2011 | Huber | A61M 15/00 128/203.12 |
| 2011/0196252 A1 | 8/2011 | Ganshorn | |
| 2011/0226242 A1 | 9/2011 | Von Hollen | |
| 2012/0029376 A1 * | 2/2012 | Meng | A61B 5/087 600/538 |

FOREIGN PATENT DOCUMENTS

| | | |
|---|---|---|
| WO | 2001058514 | 8/2001 |
| WO | 2006083014 | 8/2006 |
| WO | 2007012871 | 2/2007 |
| WO | 2007116953 | 10/2007 |
| WO | 2008016156 | 2/2008 |
| WO | 2008050542 | 5/2008 |
| WO | 2008058941 | 5/2008 |
| WO | 2009136654 | 11/2009 |
| WO | 2010052479 | 5/2010 |
| WO | 2011083377 | 7/2011 |
| WO | 2011163272 | 12/2011 |

* cited by examiner

INHALATION DEVICE WITH FEEDBACK SYSTEM

RELATED APPLICATIONS

This application is the United States national stage of International Application No. PCT/EP2012/076963, filed Dec. 27, 2012, which was published as International Publication No. WO 2013/098334 A1, and which claims benefit of European Application No. 11195773.4 filed, Dec. 27, 2011 and European Application No. 12190139.1 filed Oct. 26, 2012. All applications are incorporated by reference in their entirety herewith.

FIELD OF THE INVENTION

The present invention relates to the field of inhalation, in particular to inhalation devices and methods useful for the administration of aerosols.

BACKGROUND OF THE INVENTION

The administration of aerosolised medicines is one of the main pillars of therapy for a number of pulmonary diseases such as asthma, chronic obstructive pulmonary disease (COPD), infant respiratory distress syndrome (IRDS), pulmonary arterial hypertension (PAH) or cystic fibrosis (CF). The particular advantage of inhalation therapy is that, in principle, the aerosolised medicine is directly administered to the affected organ, i.e. the respiratory system, rather than to the systemic blood circulation from where the drug substance is distributed to the lungs, but also to other organs and tissues where the compound is not desired and can cause side effects.

However, specific delivery of aerosols by means of the inhalation route of administration is not straight-forward. The degree to which an aerosol reaches its target destination within the respiratory system depends on numerous factors, including the aerosol parameters, such as the aerodynamic diameter of the aerosolised particles or droplets, which result from the pharmaceutical composition and the inhalation devices that it used to convert the composition into an inhalable aerosol; but also on patient-related factors, such as the volume of inhalation and, in particular, the inspiratory flow rate and/or the inspiratory pressure. For example, many patients inhale at too high inspiratory flow rates and/or underpressures, assuming that "sucking in" their medication would deliver higher fractions of it into the deep lungs, and thus be most beneficial. Tiddens et al. (Journal of Aerosol Medicine; Vol. 19, Nr. 4, 2006; Pp. 456-465) describes that even patients suffering from cystic fibrosis achieve a mean peak inspiratory flow rate (PFI) of 52 L/min (range 26-70) for all patients (47 L/min (26-62) in children) at the highest resistance tested for a dry powder inhaler; minimal flow rates of 30, 45, and 60 L/min at that highest resistance were obtained in 99%, 80%, and 22% of all patients. While such high flow rates may be necessary in dry powder inhalers to disperse the powdered formulation, they are not desirable for other inhalation devices which emit a pre-dispersed aerosol and they increase the likelihood that aerosol particles or droplets impact in the throat of a patient rather than the lungs. Throat deposition not only means that the respective fraction of the therapeutic compound is lost, but also an increased risk of systemic or local side effects. In addition, when inhaling too fast through a device providing flow resistance, as is e.g. already common for dry powder inhalers, the underpressure increases. High underpressure in a patient's lung will induce a progressive constriction of small alveoli and bronchi, with the consequence that less drug can be deposited there.

Therefore, attempts are being made to train patients to perform a proper breathing manoeuvre in order to achieve appropriate deposition of the aerosol formulation. However, such training is often perceived as inconvenient by the patient and/or the health professional. Moreover, the capability of patients of complying with breathing instructions is very diverse. In particular children, elderly patients, patients with motoric difficulties or mental limitations are often not able to perform a breathing manoeuvre correctly as instructed. Thus the success of training alone is limited.

Furthermore, these issues become even more important when the number of breaths required to administer a desired dose increases. While, for example, many dry powder inhalers, pressurised metered dose inhalers and/or soft mist inhalers deliver the required dose within just one or two inhalation manoeuvres upon actuation, drug administration with most nebulisers, such as ultrasonic nebulisers, jet nebulisers and/or vibrating mesh nebulisers typically involves a larger number of inhalation manoeuvres and thus longer administration times. The risk of deviating from a trained breathing manoeuvre increases with administration time; e.g., due to distraction or getting less concentrated. Furthermore, an underpressure which may be well tolerable for one or two breaths only, e.g., inhaling at −40 mbar with a dry powder inhaler, can become rather inconvenient and exhausting when more inhalation manoeuvres are required.

To compensate for patients' difficulties and limitations, improved inhalation devices have been developed that take the capabilities of individual patients into account and provide aerosols with optimised flow and volume. For example, the AKITA® JET inhalation system, which is based on a conventional jet nebuliser in combination with a control unit that actively regulates inspiration flow as well as inhalation volume, substantially improves the deposition of an aerosolised drug in the target region compared to purely patient-controlled inhalation. Using such system also leads to a more reproducible lung deposition and thus to a more predictable therapeutic effect.

One of the limitations of such systems which control flow and volume is that they are not readily portable. It is difficult to implement the control features and functionalities within a small handheld device, which is the type of inhaler that is preferred by some patients due to its portability. Some attempts to ensure, or at least facilitate, appropriate aerosol inhalation manoeuvres, even with hand-held devices, have been described in the prior art.

EP 2 283 887 B1 discloses a miniaturised device for variable flow rate limitation at low differential pressure (or, in case of an inhalation, underpressure, or negative pressure), in particular for the limitation of the inhalation flow during the inhalation of therapeutic aerosols. While EP 2 283 887 B1 is silent as to any specific type of inhalation device such as powder inhalers, pressurised metered dose inhalers or nebulisers in which it is to be used, the device is small enough to be accommodated e.g., in a hand-held inhalation device. Depending on the geometric dimensions of the device and/or the flexibility of the membrane employed in it, among other parameters, said device for flow rate limitation (or flow rate restrictor, or flow restrictor) provides a variable flow restriction; i.e. the flow rate does not increase linearly with increasing underpressure; in other words, at a low underpressure, there is relatively less flow restriction than at a high underpressure. Depending on its configuration, such variable flow restrictor may even provide for a maximum flow rate; i.e. even if the patient tries to inhale faster and thus increases the underpressure, the flow rate does not increase much further beyond a maximum flow rate.

However, it is difficult and undesirable to rely solely on flow restriction in order to ensure a desirable low inspiratory flow rate. For example, to prevent a patient from inhaling at a flow rate of more than about 12 to 18 L/min, a flow restrictor with substantial flow resistance would have to be used, which especially patients suffering from obstructive airway diseases such as asthma or COPD may consider rather uncomfortable. Hence, it can be necessary to choose a lower flow resistance for more severely affected patients at the cost of not being able to prevent patients from using higher flow rates, e.g. up to about 25–30 L/min instead of a desired flow rate in the range of e.g., 15 L/min. Moreover, patients with less compromised pulmonary functions may intuitively react to a high flow resistance by further increasing the underpressure with which they generate inspiratory flow, causing the pressure in the device, which should preferably be not lower than about −20 mbar, to decrease to values of about −30 mbar or less. Inherently, the pressure in the patient's lungs would be even lower. As mentioned above, such pronounced underpressure is undesirable because it induces a progressive constriction of small alveoli and bronchi, with the consequence that less drug can be deposited there. Since the inhalation devices equipped with a variable flow restrictor according to EP 2 283 887 B1 do not provide any control of the underpressure, this approach does not ensure proper, reproducible inhalation manoeuvres. In addition, EP 2 283 887 B1 also does not disclose any control of other inspiratory parameters such as the inhaled volume or inspiration time.

WO 2011/083377 A1 describes a feedback and compliance device which may be coupled to a pressurised metered dose inhaler (pMDI), dry powder inhaler (DPI) or an aqueous liquid dispensing system. Nebulisers such as ultrasonic nebulisers, jet nebulisers or vibrating-mesh nebulisers are not disclosed. The device comprises sensors to sense parameters relating to the use of the apparatus, and a processing unit which is programmed to cause one or more feedback device(s) to provide information to a patient based on said sensors' output. The parameters relating to the use of the apparatus for which feedback is provided are e.g., i) correct insertion of the medication storage into the apparatus,
ii) proper shaking of the drug delivery apparatus,
iii) start of inhalation in an appropriate time after shaking,
iv) inhalation for a proper time period, and/or
v) breath hold after inhalation.

According to the flowcharts provided in the document, the preset feedback typically follows a simple, binary yes-or-no-decision, and is specifically adapted for the correct use of pressurised metered dose inhalers.

WO 2011/083377 A1 emphasises that the feedback device does not modify or interfere with the flow introduced by actuation of the medication storage. There is no provision for controlling inspiratory parameters such as inspiratory flow rate and/or underpressure.

US 2011/0226242 A1 describes a respiratory drug delivery apparatus that includes a housing for holding a source of medication, a valved holding chamber/spacer from which the patient inhales and an audible feedback device coupled thereto. The audible feedback device is a sound generator adapted to generate audible instructions in response to sensor signals caused either by manual actuation (e.g., pressing a button, removing a cap, inserting a source of medication into the housing) or in response to an event relating to the operation of the apparatus (e.g., actuation of a pressurized metered dose inhaler (pMDI), opening of a valve in the spacer, etc.). Said audible instructions may comprise pre-recorded instructions relating to shaking and actuating the pMDI, proper inhalation and holding one's breath, which either correct or prevent an incorrect use or reinforce the correct one. For example, the device may be configured to provide audible instructions for taking and counting a certain number of breaths or for inhaling for a particular period of time. Alternatively, the audible feedback device may be a noisemaker, such as a whistle or sound reed integrally formed in the holding chamber, which may start to emit a sound when the patient needs to be instructed with respect to the next action to take, or alerted to an event or a problem.

US 2011/0226242 A1 is silent about important parameters relating to the breathing manoeuvre which have substantial impact on the degree and site of drug deposition, in particular desirable ranges for inspiratory flow rates and inhaled volumes. While the document also mentions the possibility of using audible feedback to a patient to encourage slow inhalation, it is highly unlikely that such general instruction will enable a patient to actually achieve inhalation at a particular target flow rate and/or underpressure.

US 2005/087189 A1 discloses a device for the delivery of drug-laden or drug-free air during multiple inhalations. The drug delivery device comprises sensors for monitoring the breathing pattern of a patient; a processor with an internal clock to analyse said breathing pattern in order to control the onset and duration of the drug-laden and calculate the cumulative, administered dose; and a feedback indicator. The feedback indicator provides information to the patient as to whether the monitored breathing pattern is effective or suitable for inhaling drug-laden air. If the breathing pattern is too weak or too unsteady, the drug-laden pulse will not be delivered or stop early. For this purpose, the device comprises sensors which detect the onset and end of an inhalation. The device may further comprise a sensor for detecting the introduction of drug into a holding chamber.

However, US 2005/087189 A1 does not disclose any intention or means for controlling certain important parameters relating to the breathing manoeuvre, in particular a desirable inspiratory flow rate, inhaled volume, and/or underpressure.

U.S. Pat. No. 5,906,202 A describes a hand-held, self-contained and readily portable respiratory drug delivery device which is capable of measuring and recording the patient's total respiratory tract capacity, the inspiratory flow rate and inspiratory volume, e.g. by a microprocessor in combination with a read/write memory means and a flow measurement transducer. These spirometric parameters are measured in a monitoring event before the actual dosing event (also called drug delivery event) in order to calculate the time point when, during a patient's inhalation phase, to actuate the release of an aerosol bolus into the inspirational air flow, and the volume of said aerosol bolus. The actuation occurs automatically and leads to the spring-driven ejection of one or more doses of liquid drug formulation from a blister strip through a porous membrane with defined pore sizes. After the release the aerosol bolus and its inhalation by the patient, the flow can be shut off completely or partially by means of a ball valve, needle valve, gate valve or pinch valve. Alternatively, the device may provide a signal (light or sound) to the patient requesting him/her to stop inhalation.

The device may further comprise visual feedback components such as light diodes which display to the patient in a countdown fashion the remaining seconds during which breath must be held. It may also prompt the patient to hold his breath until notified by a visual signal (e.g., flashing light) or an audio signal. The device may be equipped with a flow rate sensor, and visual signals may indicate to the patient whether or not he inhales at the preferred rate.

However, it is difficult for patients to achieve a desirable low flow rate of e.g. 12 to 18 L/min on the basis of this type of feedback alone. Rather, most patients would tend to produce a substantially fluctuating inspiratory flow rate, leading to variable drug deposition and unpredictable therapeutic effect. The feedback system requires the patient to be fully concentrated on the feedback signals, which may be difficult in particular for children and elderly patients, but also for most other patients under treatment regimen which require long inhalation times.

Thus, there is an ongoing need for inhalation devices that overcome one or more of the limitations of the presently known devices. In particular, there is a need for improved inhalation devices which make it easier for patients from very different patient populations and with rather different levels of pulmonary function to perform breathing manoeuvres optimised for a specific therapeutic application, to achieve and maintain a desired inspiratory flow rate and/or to avoid applying too much underpressure when inhaling a therapeutic aerosol.

These needs are addressed by the present invention whose object is to provide such improved devices. Other needs and objects of the invention will become clear on the basis of the description and the patent claims.

SUMMARY OF THE INVENTION

The invention provides, among other things, an inhalation device for enabling a user to inhale at a desired inspiratory flow rate and/or inspiratory pressure, which is configured to guide the user to perform an inhalation manoeuvre in an optimised manner with respect to parameters such as inspiratory flow rate, inspiratory pressure, inspiration time, or inhaled volume. The inhalation device comprises a flow restrictor to restrict the air flow through the device to the patient. It further comprises a feedback system which enables the user during the inhalation manoeuvre to recognise whether he is performing the manoeuvre correctly, e.g. within a predetermined range of inspiratory flow rate and/or at a desired pressure. Moreover, the feedback system facilitates the immediate correction or adaptation of the inhalation manoeuvre by the user so as to ensure that the aerosol is inhaled and delivered to the target regions of the respiratory system.

The feedback system includes a sensing device comprising one or more sensors capable of directly or indirectly sensing an inhalation parameter, such as pressure sensors or flow sensors. The sensing device senses the actual value of the respective inhalation parameter during inhalation and generates a signal corresponding to this value.

The feedback system further includes a controller and an electronic memory. The controller receives the signal generated by the sensing device and compares it to one or more target values or target ranges stored in the memory.

Moreover, the system includes a signalling device capable of emitting one or more output signals which can be perceived by the user. The output signal may be an optical signal, an acoustic signal, a tactile signal, or any combination thereof. For example, the signalling device may comprise one or more light-emitting diodes. The controller operates or controls the signalling device in response to the signals received by the sensing device. The feedback system is configured to indicate to the user during the inhalation manoeuvre by means of the output signal(s) whether the actual value of the inhalation parameter matches the predetermined target value or range.

In one aspect of the invention, the memory stores a first target range and a second target range, the second target range being larger than and including the first target range; the signalling device is capable of emitting at least two different output signals, and the feedback system is configured to indicate to the user by means of a first output signal whether the actual value of the inhalation parameter is within the first target range and by means of a second output signal whether the actual value of the inhalation parameter is within the second target range. This is particularly advantageous when the inhalation parameter is inspiratory flow rate or inspiratory pressure.

In a further aspect, the signalling device emits light of higher intensity when the actual value of the inhalation parameter is within a target range than when the actual value is outside that target range, and/or the signalling device emits light of decreasing intensity the further the actual value of the inhalation parameter deviates from a target range. This is also particularly advantageous when the inhalation parameter is inspiratory flow rate or inspiratory pressure.

The inhalation device preferably comprises a nebulising means for converting a liquid into a nebulised aerosol. Preferably, the nebulising means is a means for continuously atomising a liquid over a period of time, such as those atomisers that are commonly used in ultrasonic or vibrating-mesh nebulisers.

The flow restrictor is preferably a variable flow restrictor capable of restricting the air flow in the device in response to pressure (i.e. the degree of underpressure).

Further aspects, embodiments and features of the invention are disclosed in the detailed description of the invention below.

DETAILED DESCRIPTION OF THE INVENTION

Figure 1:
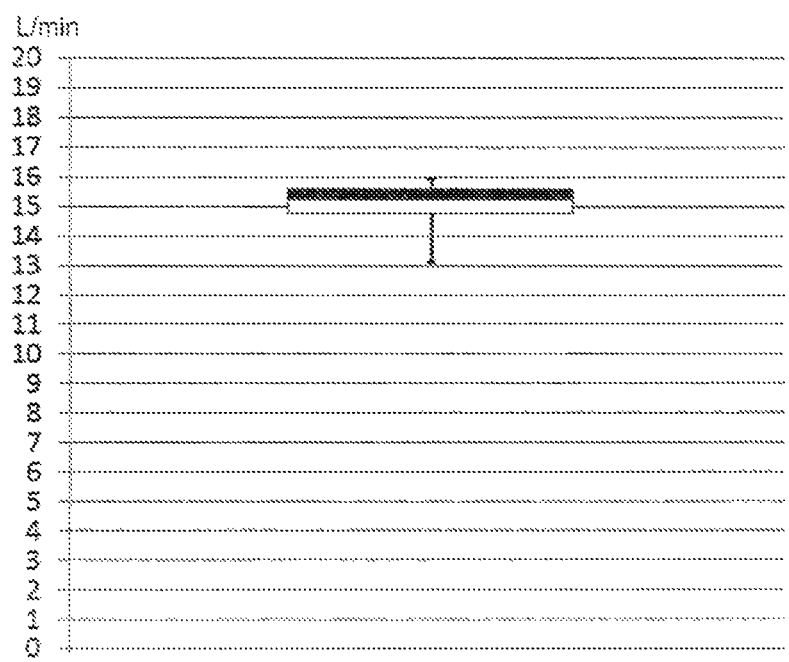
FIG. 1 shows a boxplot with the inspiratory flow rates achieved by 27 volunteer users of an inhalation device equipped with a nebulising means, a flow restrictor and a feedback system according to the invention. For further details, see Example 1.
Figure 2:
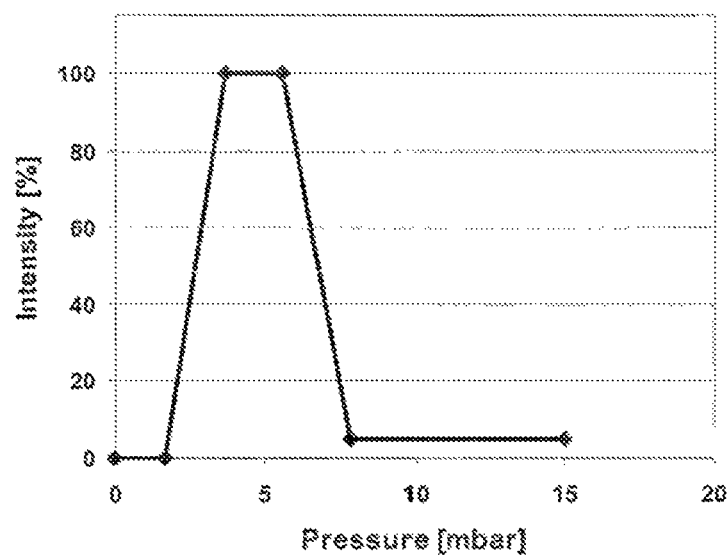
FIG. 2 shows a graph indicating the configuration of the feedback system incorporated in the inhalation device used in Example 1 with respect to the output signal, which is in this case an optical signal wherein the light intensity changes depending on the sensor signal for inspiratory flow (determined through underpressure). It is noted that the pressure values in the graph are absolute values, i.e. without the negative sign. For further details, see Example 1.
Figure 3:
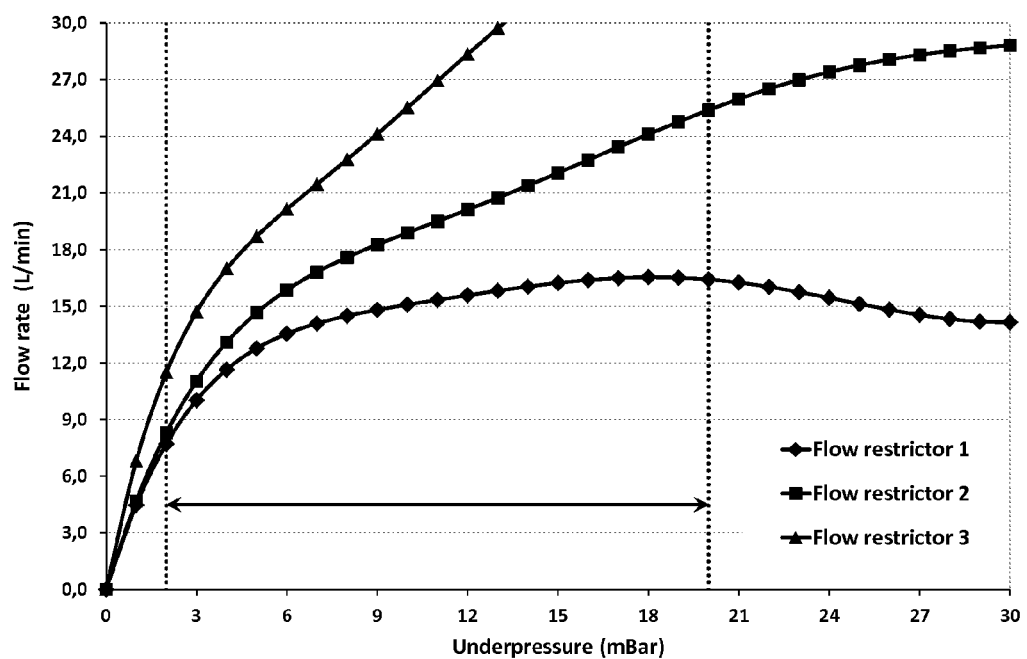
FIG. 3 shows the underpressure-flow rate graphs of three different flow restrictors together with the target inspiratory pressure range from about −2 mbar to about −20 mbar (indicated by the area between the two dotted lines). It is noted that the pressure values in the graph are absolute values, i.e. without the negative sign. For further details, see Example 2.

The invention provides an inhalation device for enabling a user to inhale at a desired inspiratory flow rate and/or inspiratory pressure, comprising a flow restrictor to restrict the air flow and a user feedback system. The feedback system comprises a sensing device, an electronic memory, a signalling device, and a controller. The sensing device is capable of generating a sensor signal in response to an actual value of one or more inhalation parameters during the inhalation manoeuvre of the user. At least one of the inhalation parameters is selected from inspiratory flow rate, inspiratory pressure and inhaled volume. The electronic memory is capable of storing one or more target ranges for the inhalation parameter. The signalling device comprises one or more signalling members, each capable of emitting at least one output signal selected from an optical signal, an acoustic signal, a tactile signal, or any combination thereof. The sensing device, the memory and the signalling device are connected to the controller which is capable of receiving the sensor signal generated by the sensor, reading the electronic memory, and controlling the signalling device. The whole feedback system is configured to indicate to a user during an inhalation manoeuvre by means of the at least one output signal whether the actual value of the inhalation parameter is within a target range.

Preferably, the inhalation device comprises a nebulising means for converting a liquid into a nebulised aerosol.

The inventors have surprisingly discovered that an inhalation device comprising a flow restrictor and a user feedback system according to the present invention allows a user to quickly and easily attain an optimised inhalation manoeuvre. Since performing an inhalation manoeuvre according to specified target ranges with respect to one or more inhalation parameters is not intuitive, the user substantially profits from the guidance received by the feedback systems. Rapid correction of a suboptimal manoeuvre during an inhalation phase means enhanced inhalation efficiency and an improved deposition pattern of the aerosol within the respiratory system of the user, thus decreasing the amount of aerosol that is wasted, increasing the amount of aerosol that is deposited at the target site where it is absorbed or where it becomes therapeutically effective, and decreasing the amount of aerosol which is deposited at other sites of the respiratory system where it could lead to undesired effects. Furthermore, rapid correction of the inhalation manoeuvre may contribute to user convenience in that it allows an optimised duration and convenience of aerosol administration.

As used herein, an inhalation device is a device capable of emitting an aerosol such as to enable a user to inhale the aerosol. An aerosol is a dispersion of a solid, semisolid or liquid phase in a continuous gaseous phase, thus including e.g. powder aerosols—pharmaceutically known as powders for inhalation—and nebulised aerosols. Inhalation devices for delivering powder aerosols are commonly described as powder inhalers. Aerosolised liquids are administered by means of various inhalation devices including nebulisers, pressurised metered-dose inhalers, and soft mist inhalers. The present invention is particularly useful in combination with a mobile or hand-held inhalation device such as a mobile nebuliser. Preferred mobile nebulisers include those types that do not depend on an external air or power supply. Among the preferred nebulisers are ultrasonic nebulisers, vibrating mesh (or vibrating membrane) nebulisers, and soft mist inhalers. The invention is particularly useful when carried out with an ultrasonic nebuliser or with an electronic vibrating mesh nebuliser. These nebulisers usually require a larger number of breaths for the administration of a dose of medicine than e.g., dry powder inhalers, pressurised metered-dose inhalers, and soft mist inhalers. Large volumes of an inhalable drug composition can only be administered by nebulisers. Typically, ultrasonic nebulisers or vibrating mesh nebulisers operate continuously over the course of a few breaths up to about 45 min, emitting aerosol either constantly or in pulses which are adapted to the user's breathing pattern; e.g., triggered by the onset of inhalation. The specific treatment time and/or number of breaths required depend on parameters like the overall condition of the patient, the dose to be administered and the output efficiency of the inhalation device. For many patients, it is not easy to focus on the correct performance of their breathing manoeuvres over long inhalation times.

As used herein, a nebuliser is a device capable of converting a liquid into an inhalable aerosol using a nebulising means (or atomising means, or aerosol generator), for example a piezo-electrically driven vibrating mesh assembly. In some cases, said droplets may solidify to minute powder particles upon evaporation of the liquid carrier. As used herein, an inhalation device comprising a nebulising means is to be understood as a continuously operating device which emits the nebulised aerosol either constantly or in phases adapted to the breathing pattern of the user. For example, the generation of aerosol by the nebulising means could be inhalation triggered. The duration of the aerosol pulse may also be adapted to the patient's breathing pattern and/or lung function parameters, ranging from rather short nebulisation phases, such as 1 second, to longer nebulisation phases, such as up to 8 seconds. Relatively long nebulisation phases are often preferred, since they allow a reduction of the number of breaths required in order to administer a specific dose. Nebulisers differ from inhalation devices which emit metered aerosols only upon actuation and within a very short time frame of few milliseconds, such as devices driven by a compression spring.

As used herein, the terms patient and user are used synonymously and interchangeably, and refer to the user of an inhalation device. The term patient does not necessarily imply that the respective person suffers from any acute symptom or disease. The inhalation device according to the present invention may be used in therapeutic settings, but also for the inhalative administration of prophylactic or diagnostic formulations.

According to the invention, the inhalation device comprises a flow restrictor and a feedback system. Preferably it also comprises a nebulising means, so that the inhalation device represents, or comprises, a nebuliser. Optionally, the nebuliser is an ultrasonic nebuliser or a vibrating mesh nebuliser. Vibrating mesh nebulisers are also referred to as vibrating membrane nebulisers.

The flow restrictor to restrict the air flow is preferably responsive to the inspiratory pressure. As used herein, inspiratory pressure is the air pressure as measurable in the inhalation device at the mouthpiece during the inhalation phase of a breathing manoeuvre. The pressure may be positive or negative. Most inhalation devices require that the patient generates the inspiratory flow that is required for inhaling the aerosol emitted by the device. To generate the flow, the patient "sucks" at the mouthpiece, i.e. by creating a negative pressure (or underpressure), e.g. through the movement of the diaphragm.

As used herein, "responsive to the inspiratory pressure" means that the flow restrictor exerts a flow resistance which is not constant, but variable in response to the inspiratory pressure. As a consequence, the inspiratory flow rate will not correlate linearly with the inspiratory pressure. Preferably, the flow restrictor is configured to exert an increasing flow resistance the more negative the inspiratory pressure is. Optionally, the flow restrictor is configured to increase the flow resistance so substantially that a predefined maximum flow rate cannot be exceeded even at a strongly negative pressure (i.e. a strong underpressure generated by the patient).

An example of a flow restrictor which is particularly useful for an inhalation device according to the present invention is described in EP-A 2 283 887, which is incorporated herein by reference. The flow restrictor is miniaturised and may be accommodated even in small, hand-held inhalation devices. The flow resistance characteristics of this flow restrictor depend on e.g. the geometric dimensions, such as length of the air flow channel within the flow restrictor and the diameter of its air inlet and outlet openings; and on the material properties of the flexible wall within the flow restrictor; and during inhalation on the underpressure applied by the user.

Optionally, the flow resistance of the flow restrictor is chosen in such a way that its maximum flow rate is similar to a desired inspiratory flow rate, i.e. the target range. The target range may be narrow, such as a target value, or it may be somewhat broader, such as +/−20% of a particular value.

Alternatively, the flow resistance of the variable flow restrictor is chosen in such a way that the maximum flow rate is higher than the desired inhalation flow rate range and/or value.

It was found by the inventors, that, for example, a flow restrictor according to EP-A 2 283 887 with a maximum flow rate of 15±3 L/min had a flow resistance which many users still found tolerable and comfortable. However, patients suffering from obstructive airway diseases reported difficulties due to this flow resistance; some felt more comfortable with flow restrictors providing lower resistance, which however correspond to maximum flow rates which are higher than usually desirable, e.g. about 25-30 L/min.

As described earlier, low inspiratory flow rates such as the above mentioned, exemplary and non-limiting target range of 15±3 L/min are beneficial for the targeted delivery of aerosols into the deeper lungs, with only a minor fraction of aerosol particles deposited in the throat and/or upper airways. However, to actually reach the small structures of the deeper lungs, such as the alveoli or small bronchi, it is may also be important to avoid constriction of these structures by inhalation-induced underpressure. It was, for instance, found by the inventors that users who inhale very strongly through an inhalation device with a flow restrictor often reach pressures of −30 mbar or more (i.e. more negative). For these patients, even though inhaling at a desirable flow rate of e.g. 15±3 L/min due to the flow restrictor, such breathing manoeuvre is not optimal as the pronounced underpressure is not only very inconvenient and exhausting, but potentially also causes irritation of the respiratory system and a constriction of small lung structures. These negative effects are easily avoided through the feedback system according the invention. The feedback system may be configured to guide the user to use an optimal inspiratory pressure which is sufficient (i.e. sufficiently negative) to maintain the desired inspiratory flow rate but not much lower than (i.e. not much more negative) than required.

The difficulties of patients that are severely affected by e.g. asthma or COPD with certain flow resistance levels can be overcome, if necessary, by the use of a flow restrictor with lower resistance characteristics. Such lower resistance and the corresponding higher maximum flow rates have the effect that, in principle, a user may inhale the aerosol at higher inspiratory flow rates than desirable for optimal drug deposition. Especially in cases where the patient's lung function improves during the course of an aerosol administration, patients may gradually inhale faster. This is, however, prevented by the feedback system according to the invention, which guides the user to stay within the target range of the flow rate.

The user feedback system is any combination of components and/or devices capable of providing, during the course of an inhalation manoeuvre, an indication to the user as to how the manoeuvre is being performed. Based on the feedback, the user is enabled to modify his inhalation manoeuvre as appropriate. According to the invention, the system includes at least a sensing device, an electronic memory, a controller, and a signalling device.

The feedback may, for example, indicate to the user whether the inspiratory flow rate and/or inspiratory pressure is within the optimal range or outside of that range. If outside the optimal range, it may also give the user an approximate indication of how far away from the optimal range the manoeuvre is being performed. Moreover, the feedback may indicate that a certain inhalation volume has been reached, or that a certain inspiration time has elapsed.

The sensing device, which is capable of generating a sensor signal in response to the actual value of an inhalation parameter, should preferably include one or more pressure sensors, flow sensors, velocity sensors, temperature sensors, microphones, or any combination thereof. In particular, pressure sensors and flow (or velocity) sensors are useful for directly or indirectly determining the inspiratory flow rate during the inhalation manoeuvre. The flow rate may also serve as the basis for determining the inhaled volume (or inhalation volume) at any time. In addition, the feedback mechanism may include a clock or timer capable of generating a time signal that can be received by the controller, and it may be configured to indicate to the user, during an inhalation manoeuvre, by means of an output signal that a predetermined period of time, e.g., the desired inhalation time, has elapsed.

The sensor (or sensors) may be accommodated in various positions within the inhalation device. Obviously, a flow or velocity sensor should be located within the flow channel or air pathway of the device. A pressure sensor should also be positioned in the flow channel, or at least in a void that corresponds with the flow channel. Preferably, the inhalation device includes at least one pressure sensor capable of sensing the inspiratory pressure. Depending on the flow resistance profile of the flow restrictor and the actual value of the inspiratory pressure, the inspiratory flow rate may also be calculated from the inspiratory pressure.

The electronic memory is capable of storing one or more target ranges for the inhalation parameter. Optionally, it may store target ranges for several inhalation parameters simultaneously. As used herein, a target range is a predetermined range of values for a parameter which is considered desirable, e.g. from the therapeutic perspective, with respect to a particular user or patient, and in view of a particular therapeutic treatment. In the context of the invention, a target range, if appropriate, may be rather small in that it only consists of a particular target value, or it may be rather broad in that it only defines a lower or upper limit, the other limit being indefinite. In many other cases, the target range includes a lower limit and an upper limit.

For example, the electronic memory may store a certain target range for the inspiratory flow rate, such as from 12 to 18 L/min (i.e. 15±3 L/min), for the inspiratory pressure, such as from about −2 mbar to about −20 mbar, and/or for the inhalation volume, such as at least 750 mL. In a further embodiment, it may store an additional, broader target range for the inspiratory flow rate and/or inspiratory pressure, the broader range encompassing the more narrow range. For example, the broader range, such as from 1 to 30 L/min in the case of the inspiratory flow rate, may represent the operational range, and the feedback system may be configured to give the user an indication that he is performing the inhalation manoeuvre within the operational range; whereas the more narrow range, such as from 12 to 18 L/min, may represent the optimal range, and the feedback system may be configured to give the user an indication that he is performing the inhalation manoeuvre within the optimal range.

If the inhalation parameter is inspiratory pressure, the broader range may, for example, be from −2 mbar to −20 mbar, and the more narrow range may, for example, be from −3 mbar to −8 mbar. Optionally, a first feedback signal may indicate to the user that the inspiratory pressure is within the broader range, but outside the more narrow range, and a second feedback signal may indicate that the inspiratory pressure is within the more narrow range.

In addition, the feedback system may indicate when a target inhalation volume has been reached.

If a pressure sensor is used to determine the flow rate indirectly, the target range may also be stored in form of the pressure values (P) corresponding to the respective flow rates, e.g. $P_{12\,L}$ (for a flow rate of 12 L/min) and $P_{18\,L}$ (for a flow rate of 18 L/min). The exact correlation of these values is specific for each type of flow restrictor employed. Alternatively, a pressure value $P_{15\,L}$ (the pressure corresponding to the flow rate of 15 L/min), may be determined for a specific flow restrictor employed; and the pressure target range may be defined as e.g., $P_{15\,L}\pm3.5$ mbar.

The memory may be any type of electronic data storage device or semiconductor memory, whether volatile or nonvolatile. Examples of volatile memories include static and dynamic random-access memories; their use requires that the electric power is maintained as long as the information stored in the memory is needed. In a specific embodiment, the memory is non-volatile, such as a flash memory, a ferroelectric or a magnetoresistive random-access memory. The memory is optionally removable, such as integrated in a chip or microchip, and incorporated in a portable carrier such as a chip card.

The controller is any type of controller, microcontroller or microcomputer comprising an electronic processor core within an integrated circuit that is capable of receiving the sensor signal generated by the sensor, reading the electronic memory, and controlling the signalling device. It is important that the controller is configured to perform these operations during the inhalation manoeuvre, and that an output signal is provided to the user shortly after the commencement of the manoeuvre. To reduce the effect of short fluctuations of a sensor signal, whether such fluctuations are through electronic noise or in response to actually fluctuating values for the inhalation parameter, it may be useful to determine the actual values, which are to be compared to the target range, over a certain period of time within which the sensing devices generates a plurality of sensor signals. For example, the actual values may be determined over 50, 100, 200, or 500 milliseconds, i.e. on the basis of the averages of the sensor signals received within such period.

The signalling device may comprise one or more signalling members, each capable of emitting an output signal perceivable or recognisable by the user. The output signal may be an optical signal, an acoustic signal, a tactile signal, or any combination thereof. The output signal may also be referred to as feedback signal. In a specific embodiment, the output signal is an optical signal, and the signalling device is capable of emitting light intermittently, emitting light of different wavelengths, and/or emitting light of different intensity. A useful signalling member for emitting an optical signal is, for example, a light-emitting diode or a laser diode.

As mentioned, the feedback system is configured to indicate to the user during an inhalation manoeuvre by means of the output signal whether the actual value of the inhalation parameter is within a target range. In practise, this can be done in various different ways. For example, the system may be configured in such a way that the signalling device emits an output signal when the actual value of the inhalation parameter is outside the target range, but no signal when the actual value is within the target range. In a particular embodiment, for instance, the inhalation parameter is the inhaled volume and the target range is defined by means of a lower limit or minimum, and the output signal is light (e.g., constant or intermittent light). In this case, the light would be switched off immediately when the target volume has been inhaled by the user, thus guiding him to terminate the inspiratory phase of the inhalation manoeuvre.

Alternatively, the system may be configured to emit an output signal when the actual value of the inhalation parameter is within the target range, but no signal when the actual value is outside the target range. According to this type of configuration, the feedback system may indicate to the user by means of a blinking or constant light, for example, that he is inhaling with an optimal inspiratory flow rate and/or inspiratory pressure, i.e., with an inspiratory flow rate and/or pressure that is within the respective target range stored in the memory; or, if a broad target range of the inspiratory flow rate and/or pressure is defined as the operational flow rate and/or pressure, the signal would indicate to the user that he is now performing the manoeuvre within the operating—even though not necessarily optimal—flow rate and/or pressure range. As soon as the actual flow rate and/or pressure value is outside the target range, the light signal would be switched off, so that the user is guided to correct his manoeuvre.

In another embodiment, the configuration provides that the signalling device emits a first output signal when the actual value of the inhalation parameter is within a target range and a second output signal when the actual value of the inhalation parameter is outside that target range, the second output signal differing from the first. By way of an example for this configuration, if the inhalation parameter is the inspiratory flow rate, then the signalling device could indicate by means of a first light signal, e.g. a red light or an intermittent green light, that the actual flow rate value is outside the target range, and by a different signal, e.g. a constant green light, that the actual flow rate is now within the target range, thus giving the user immediate and clear guidance.

In a further particular embodiment, the memory stores two different target ranges for the same parameter simultaneously, e.g. a rather broad target range for the inspiratory flow rate defining the operational range along with a more narrow target range (within the broader range) defining the optimal inspiratory flow rate. In this case, it is useful to provide the inhalation device with a signalling device that is capable of emitting at least two different output signals, and to configure the feedback system so that a first output signal is emitted, e.g., an intermittent green light, while the actual flow rate is within the first (i.e. operational) target range, while a different output signal, e.g., constant green light, is emitted when the actual flow rate is within the second (i.e. optimal) target range. The second output signal may replace or supersede the first signal, or it may be emitted in addition to the first signal.

Similarly, two different output signals may be used in order to guide the user with respect to two different inhalation parameters. For example, a first signal may indicate that the actual inspiratory flow rate is within the target range, while a second and different signal indicates when the target inhalation volume has been reached. More specifically, a constant green light may be used to indicate an optimal inspiratory flow rate, and a blinking red light may be used to indicate that the target volume has not yet been reached.

In a similar manner, a constant green light may be used to indicate an optimal inspiratory flow rate, whereas e.g. an orange or red light (or any other colour clearly discernible from green) may be switched on if the negative pressure is below a predefined limit. The user may be instructed by the inhalation device's manual and/or physician, prior to first use, to inhale with just as little effort as is required to achieve the target range of the inspiratory flow rate, as indicated by e.g. a constant green light.

In addition, the feedback system may be configured to emit an output signal to indicate an error. For example, a blinking red light may be used for this purpose, e.g., to indicate a low battery status, negative inspiratory flow (i.e. expiration), incorrect or incomplete device assembly, absence of target ranges, an empty drug formulation reservoir etc.

Any combinations of the embodiments described above are also considered. For example, a blinking light of one wavelength (e.g., red) may be used to indicate that the actual inspiratory flow rate and/or pressure is within the (broadly defined) operating range and at the same time to indicate that the target inhalation volume has not yet been reached; once it is reached, the blinking light will be switched off. In parallel, a constant light of another wavelength (e.g., green) is emitted to indicate when the actual inspiratory flow rate and/or pressure is within the (more narrowly defined) optimal range.

As mentioned above, the output signal, or one or more of the output signals, may also be an acoustic or a tactile signal. For example, it may be useful to use a non-optical signal to indicate whether the actual value of a first inhalation parameter is in a target range, and an optical signal to indicate whether the actual value of a second inhalation parameter is in a target range, and/or whether the actual value of a first inhalation parameter is in a second target range. According to this embodiment, a non-optical signal, such as a sound or vibration, may be used to indicate when the actual inhalation volume has reached the target range or target volume or if the inspiratory pressure is below a predefined limit, and a light signal may be used to indicate when the actual inspiratory flow rate and/or pressure is within a target range. The particular advantage of this group of embodiments is that the user does not have to differentiate between different signals of the same type, e.g., different optical signals, which requires even less attention and coordination, and minimised the risk of confusion. Thus, even mentally impaired patients—depending on the degree of impairment—, as well as young children or elderly users with coordination problems will be effectively guided by the feedback system to perform an overall correct or adequate inhalation manoeuvre.

In a further specific embodiment which is particularly advantageous, the output signal that is used to indicate to the user whether the actual inspiratory flow rate and/or the inspiratory pressure is within a target range defining the optimal flow rate is light of varying (or different) intensity. In particular, the feedback system may be configured so that the signalling device emits light of higher intensity while the flow rate and/or pressure is in the optimal range; and light of lower intensity (but preferably of the same wavelength) when the flow rate and/or the pressure is outside the optimal range, or target range. Moreover, the intensity of the light signal may also vary outside the target range depending on the difference between the actual flow rate and/or pressure and the target range. In other words, the signalling device emits light of decreasing intensity the further the actual value of the inhalation parameter deviates from a target range. The variation in intensity may be continuous or incremental. It has been found by the inventors that this type of configuration is most easily interpreted by different users, allowing them to react quickly, easily, and in the right manner, such as to immediately correct their inhalation manoeuvre while inhaling and breathe with an optimal flow rate and/or pressure. Even untrained users who have previously never used an inhalation device are instantly capable of performing an optimal inhalation manoeuvre when guided by the feedback system in this particular configuration.

In analogy, a variable non-optical signal may be used instead of light of variable intensity to provide feedback to the user with respect to degree of deviation of the inhalation parameter from the target range or value. For example, a sound signal used as output signal may have different levels of pitch (i.e. audio frequency) or intensity (i.e. volume), depending on how much the inhalation parameter—in particular the inspiratory flow rate and/or pressure—differs from the target range. More specifically, the pitch or the sound volume may be configured to increase stepwise or continuously until the user achieves the target flow rate and/or pressure; if the user then does not stay within the target range but exceeds, or falls short of, the target range again, the pitch or the sound volume decreases stepwise or continuously in proportion to the degree of deviation from the target range.

Using light of different intensity, or a non-optical output signal of variable intensity or wavelength, for guiding a user to apply an optimal inspiratory flow rate and/or pressure may of course be combined with other optical and/or non-optical signals to guide the user with respect to the operational flow rate, the pressure, the inhalation time or the target volume to be inhaled, or all of these. For example, if the actual flow rate is outside the broad operating range, the light signal whose intensity normally indicates whether and how far the flow rate is outside the optimal range may be switched off altogether. Alternatively, light of a different wavelength, intermittent light, or a sound, or any other signal may be used to provide guidance with respect to the operating range. In addition, such another signal may be used to indicate that the target inhalation volume has been reached.

In a particular embodiment, the feedback system comprises one or more signalling members capable of emitting an optical signal arranged in such a way that they are not directly visible by the user; instead, they are positioned so that the user receives diffused light. In this way, the optical signal will not irritate the eyes of the user. In general, it is more convenient or pleasant to the user if a light signal is received indirectly, e.g. by means of an illuminated surface that reflects the light signal, or through an optically opaque or translucent material which absorbs and/or scatters at least some of the emitted light.

It is recommended that the surface that reflects the light, or transmits and scatters the light, extends over at least about 0.5 cm$^2$, in particular over at least 1 cm$^2$. In further embodiments, that surface extends over at least 2 cm$^2$, or at least 3 cm$^2$, or at least 5 cm$^2$, respectively. Moreover, for the sake of user convenience, it may also be useful to position the illuminated surface, or surfaces, in a peripheral region of the user's field of vision when holding the device inhalation properly.

A useful way of achieving this is by positioning the optical signalling device, e.g., comprising a light-emitting diode as a signalling means, in such a way that it illuminates the mouthpiece, or a part of the mouthpiece, of the inhalation device. For example, the signalling device may be incorporated inside the inhalation device within or near the mouthpiece, and the mouthpiece itself may be made from an opaque or translucent material such as polypropylene. As already mentioned, the signalling device may comprise more than one signalling means, e.g. two or more light-emitting diodes; these may be arranged on both the left and the right side of the central axis of the flow channel inside the mouthpiece. For example, two pairs of light-emitting diodes may be used, each pair emitting the same wavelength, but the second pair emitting a different wavelength than the first pair; a useful way of arranging these within the device is to place one member of each pair on the left-hand side and the other member of each pair on the right-hand side of the central axis of the flow channel within the mouthpiece, so that each of the respective light signals is conveniently recognised by the user through both of his eyes.

In yet a further embodiment, the inhalation device comprises a shut-off feature capable of interrupting the air flow in the device. Preferably, the shut-off feature is controlled by the controller in response to a sensor signal received from the sensing device and/or to a time signal received from the timer. For example, the air flow may be shut off or limited to an infinitely small flow rate when the target value or target range for the inhalation time or inhalation volume has been reached.

Moreover, the invention is also directed to a method for inhaling an aerosol. The method is characterised in that it includes an inhalation device as described above. Also within the scope of the invention is a method of treating a patient in need of such as treatment, wherein the method comprises a step of administering an aerosol using the inhalation devices as described herein.

Figure 5:
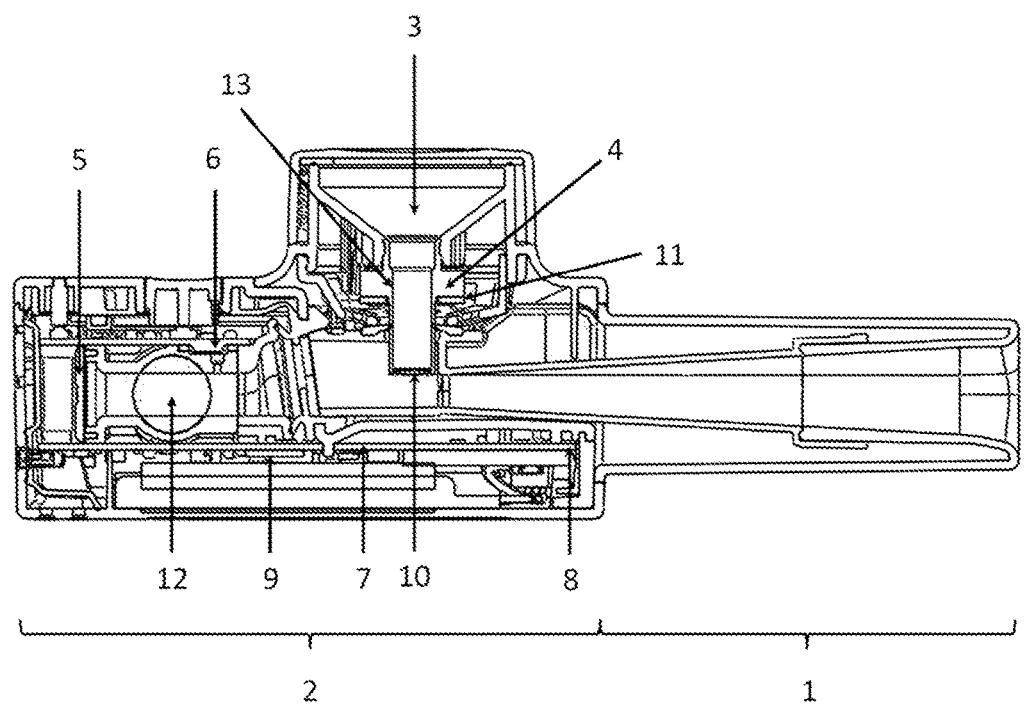
FIG. 5 shows a cross-section of a particular embodiment of an inhalation device according to the present invention.
Figure 6:
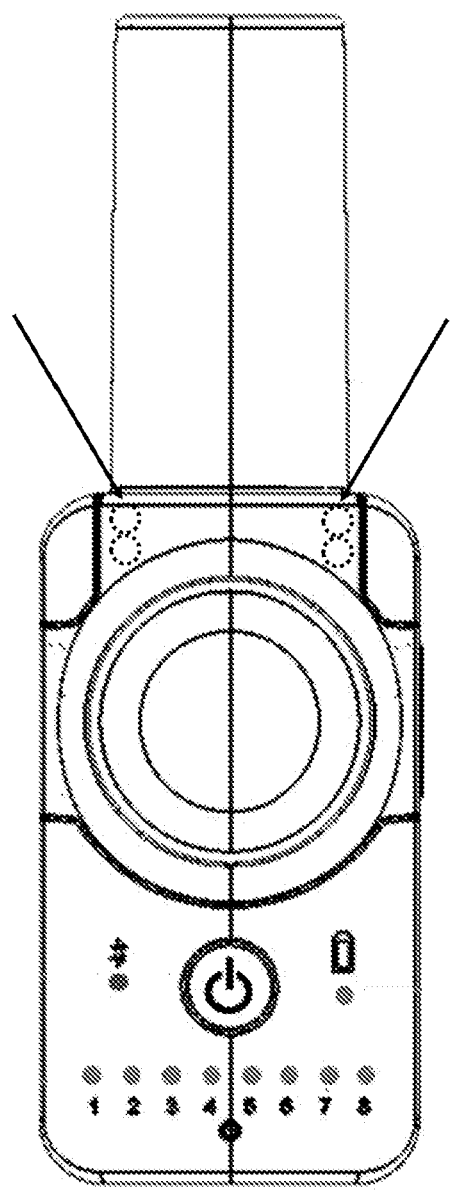
FIG. 6 shows a top view of a particular embodiment of an inhalation device according to the present invention, with the arrows indicating the exemplary position of signalling members, such as light emitting diodes.

One particular embodiment of such an inhalation device according to the present invention is depicted in FIG. 5. This device is a hand-held nebuliser, of which a cross-section is shown. The device comprises a mouthpiece (1) and a base unit (2), a reservoir (3) for a liquid formulation to be nebulised, a nebulising means (4), the flow restrictor (5), and a user feedback system. The feedback system comprises a sensing device (6) in fluid connection with the air flow channel; an electronic memory which forms an integral part of the mother board (7); a signalling device (8); and a controller (9). In this particular embodiment, the mouth piece (1) is made from a translucent, opaque material such as translucent polypropylene and the signalling device (8) comprises four light emitting diodes (LEDs); more specifically, two sets of one green and one orange LED each, located at the front end of the mother board (7) and to the left and right of the mouthpiece (1) (i.e. perpendicular to the cross-section shown in FIG. 5), so as to illuminate the mouthpiece with diffused light. The position of the LEDs is also indicated by the arrows in FIG. 6 which shows the top view of this particular inhalation device. In this embodiment, the nebulising means (4) is vibrating mesh assembly, comprising the vibrating mesh (10) at the downstream end of a piezoelectric transducer body (13) and a piezo-element (11) for vibrating the mesh (10) in order to generate an aerosol of minute liquid droplets into the air flow channel. In this particular embodiment, the inhalation device further comprises a shut-off-valve (12) capable of interrupting the air flow, once a predetermined inhalation volume and/or inhalation time has been reached.

The invention further encompasses the following embodiments:

(1) An inhalation device with a user feedback system, said feedback system comprising:
  (a) a sensing device capable of generating a sensor signal in response to an actual value of an inhalation parameter during the inhalation manoeuvre of the user, said parameter being selected from inspiratory flow rate and inhaled volume;
  (b) an electronic memory capable of storing one or more target ranges for the inhalation parameter;
  (c) a signalling device capable of emitting an output signal; and
  (d) a controller capable of receiving the sensor signal generated by the sensor, reading the electronic memory, and controlling the signalling device;
  wherein the feedback system is configured to indicate to a user during an inhalation manoeuvre by means of the output signal whether the actual value of the inhalation parameter is within a target range. An inhalation device according to the invention, wherein the signalling device emits no output signal when the actual value of the inhalation parameter is within a target range, and wherein the signalling device emits an output signal when the actual value of the inhalation parameter is outside that target range.

(2) An inhalation device according to embodiment (1) above, wherein the memory stores a first target range and a second target range, the second target range being larger than and including the first target range, and wherein the signalling device is capable of emitting at least two different output signals; and wherein the feedback system is configured to indicate to the user by means of a first output signal whether the actual value of the inhalation parameter is within the first target range and by means of a second output signal whether the actual value of the inhalation parameter is within the second target range.

(3) An inhalation device according to embodiment (1) above, wherein the memory stores a first target range for a first inhalation parameter and a second target range for a second inhalation parameter, and wherein the signalling device is capable of emitting at least two different output signals; and wherein the feedback system is configured to indicate to the user by means of a first output signal whether the actual value of the inhalation parameter is within the first target range, and by means of a second output signal whether the actual value of the inhalation parameter is within the second target range.

(4) An inhalation device according to any of embodiments (1) to (3) above, wherein the sensing device comprises is a pressure sensor, a flow sensor, a velocity sensor, a temperature sensor, a microphone, or any combination thereof.

(5) An inhalation device according to any of embodiments (1) to (4) above, wherein the output signal of the signalling device of said inhalation device is optical, such as a light-emitting diode or a laser diode, and wherein the output signal is light, and wherein the signalling device of said inhalation device is capable of
 (a) emitting light intermittently,
 (b) emitting light of different wavelengths, and/or
 (c) emitting light of different intensity.

(6) An inhalation device according to embodiment (5) above, wherein at least one signalling members of the signalling device is a light-emitting diode or a laser diode capable of emitting light intermittently, emitting light of different wavelengths, and/or emitting light of different intensity and wherein said signalling members are not directly visible by the user, but arranged such that the user receives diffused light.

(7) An inhalation device according to embodiment (5) above, wherein at least one signalling members of the signalling device is a light-emitting diode or a laser diode capable of emitting light intermittently, emitting light of different wavelengths, and/or emitting light of different intensity and wherein said signalling members are not directly visible by the user, but arranged such that the user receives diffused light, wherein said inhalation device further comprises a mouthpiece which is associated with the signalling device and/or illuminated by the optical signal; and wherein optionally at least a part of the mouthpiece is made from a translucent material such as polypropylene.

(8) An inhalation device according to embodiment (5) above, wherein at least one signalling members of the signalling device is a light-emitting diode or a laser diode not directly visible by the user, but arranged such that the user receives diffused light, and wherein said inhalation device further comprises an at least partially translucent mouthpiece illuminated by the optical signal; and wherein the signalling device emits light of higher intensity when the actual value of the inhalation parameter is within a target range than when the actual value is outside that target range, and/or wherein the signalling device emits light of decreasing intensity the further the actual value of the inhalation parameter deviates from a target range.

(9) An inhalation device according to embodiment (5) above, wherein at least one signalling member of the signalling device is a light-emitting diode or a laser diode not directly visible by the user, but arranged such that the user receives diffused light, and wherein said inhalation device further comprises an at least partially translucent mouthpiece illuminated by the optical signal; and wherein the signalling device emits light of a first wavelength when the actual value of the inhalation parameter is within a target range, and light of a second wavelength which is different from the first wavelength when the actual value of the inhalation parameter is outside the target range.

EXAMPLE 1

A hand-held nebuliser according to the present invention comprising a vibrating mesh-type aerosol generator, a flow restrictor and a user feedback system was configured and tested as follows. The flow restrictor was responsive to the inspiratory pressure. The inhalation parameter was the inspiratory flow rate, whose target range was set at 15±3 L/min. A pressure sensor was incorporated within the flow channel such as to measure the inspiratory pressure and indirectly determine the inspiratory flow rate. The signalling device comprised light-emitting diodes (LEDs) capable of emitting green light of variable intensity. Two sets of LEDs were incorporated inside the device such as to illuminate the mouthpiece, which itself was made from translucent polypropylene. The feedback system was configured to emit green light to illuminate the mouthpiece with the highest intensity when the inspiratory flow rate is within the target range. This flow rate was determined via a pressure value measured with a pressure sensor. By having the flow-pressure characteristic with the device in form of a look-up table, the flow rate was determined. A flow rate of 15±3 L/min corresponded to, or was achieved at, a pressure of −3.7 to −5.6 mbar at the mouthpiece. Outside this target range, but within the operational range (i.e. a second and broader target range for the same inhalation parameter), the signalling device would emit green light of less than 100% of the maximum intensity. With decreasing negative pressure (i.e. below −5.6 mbar), the light intensity decreased, until the intensity reached a plateau of 5% light intensity at a pressure of −7.9 mbar and below. With increasing negative pressure at the mouthpiece at values higher than −3.7 mbar, light intensity also decreased until reaching 0% at a pressure of −1.7 mbar.

FIG. 2 shows how the light intensity was configured to change in response to the inspiratory flow as determined through the negative pressure value for the specific variable flow restrictor employed. It should be noted that the graph shows the absolute values (or moduli) for the pressure, and does not show the negative sign. The purpose of not reducing the light intensity to 0% but 5% instead for negative pressures with values on the right of the target range, i.e. "above" 7.9 mbar underpressure (i.e. below −7.9 mbar), is to let the user know that inhalation is too fast rather than too slow.

27 Volunteers (21-72 years of age), of which 13 had no previous experience with nebulisers or other inhalers, were asked to perform 20 inhalation manoeuvres using the experimental device, without any further explanations given to the volunteers. In result, nearly all volunteers, guided by the feedback system, inhaled with an inspiratory flow rate very close to 15 L/min, with a remarkably low degree of variability as indicated in FIG. 1.

EXAMPLE 2

A hand-held nebuliser similar to Example 1 was used to test three different flow restrictors, all of which were responsive to inspiratory pressure. Again, 27 volunteers (21-72 years of age), of which 13 had no previous experience with nebulisers or other inhalers, were asked to perform 5 inhalation manoeuvres using the experimental device, with a short explanation given to the volunteers that they should aim for a green light at maximum intensity and adjust their inhalation accordingly if light intensity decreases.

FIG. 3 shows the underpressure-flow rate graphs of the three flow restrictors together with the target pressure range from about −2 mbar to about −20 mbar (indicated by the area between the two dotted lines). With all three devices, the flow resistance increases with increasing absolute value of the negative pressure, as indicated by the relatively smaller increase of the corresponding flow rate at high absolute pressure values. The higher the gradient of the curves, the lower the overall resistance profile of the flow restrictor. It should be noted that with a flow restrictor with a very low flow resistance profile, such as flow restrictor 3, the target pressure range corresponding to a specific target flow rate range like 12 to 18 L/min, is rather narrow and more difficult for the user to maintain. Higher overall flow resistance profiles, such as with flow restrictor 1, are capable of physically limiting the inspiratory flow rate to a maximum, thus preventing flow rates that are too high for optimal drug deposition. However, they bring about a higher risk that a user will apply too much underpressure, for example in response to the impression that the inspiratory flow rate is too low. With an inspiratory pressure below about −20 mbar (i.e. with an underpressure above 20 mbar), the user would still inhale at a desired flow rate but at the cost of convenience. Moreover, there is a potential for constriction of fine structures in the deeper lungs. Intermediate overall flow resistance profiles, as e.g. with flow restrictor 2, provide a compromise. The flow resistance is low enough to be comfortable even for patients more severely affected by constrictive airway diseases like asthma or COPD. However, if the patients increase their inhalation efforts, and thus underpressure, they might inhale faster than desirable, i.e. outside of the exemplary target range of 12 L/min to 18 L/min.

Figure 4:
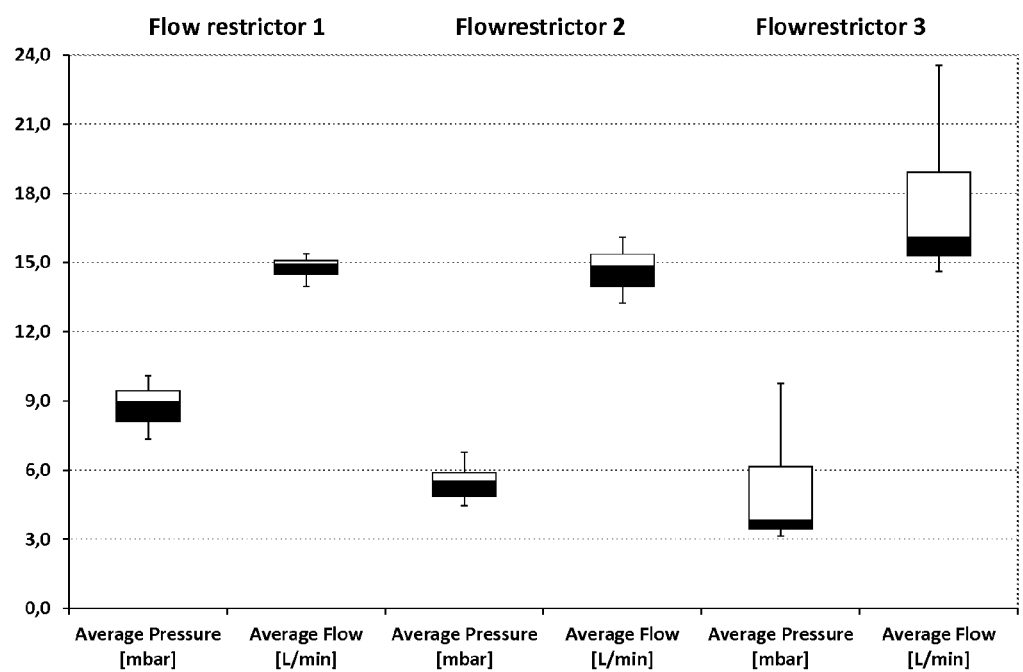
FIG. 4 shows boxplots of the inspiratory flow rates and underpressures achieved during 5 breaths by 27 volunteer users of an inhalation device according to the invention equipped with a nebulising means, a feedback system and three different flow restrictors. It is noted that the pressure values in the graph are absolute values, i.e. without the negative sign. For further details, see Example 2.

FIG. 4 shows boxplots of the inspiratory flow rates and underpressures achieved by the 27 volunteers. With flow restrictor 1, volunteers inhaled in average at −9 mbar inspiratory pressure to generate a mean constant flow rate of about 15 L/min. The variability was very low, i.e. from −7.5 mbar to −10 mbar for the inspiratory pressure, which pressure values ensured that all users achieved the target flow rate of 15±3 L/min. The feedback system successfully prevented inhalation at too high underpressure values while the maximum flow rate of flow restrictor 1 prevented flow rates above 16 L/min.

With flow restrictor 2, all volunteers inhaled in average at a lower underpressure of −5.5 mbar to generate a flow rate of about 15 L/min. The low variability of the inspiratory pressure between −4.5 mbar and −7 mbar is compatible with the target flow rate range of 15±3 L/min. While this flow restrictor would have allowed for much higher flow rates, these were successfully prevented by the feedback system.

With flow restrictor 3, volunteers inhaled at an even lower average pressure of −3.8 mbar, with individual pressure values ranging from −3.2 to −10 mbar. In spite of the steep gradient of the underpressure-flow rate curve of the flow restrictor, the volunteers still achieved an average flow rate close to 15 L/min, owing to the effective feedback system according to the invention, even though the variability was somewhat higher than with flow restrictors 1 and 2. It is noted that without the feedback system, the average flow rates generated by users with this device are typically much higher, i.e. far above 20 L/min, and associated with substantially higher variability (data not shown).

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. An inhalation device for enabling a user to inhale at a desired inspiratory flow rate and/or inspiratory pressure, comprising
    (a) a flow restrictor to restrict the air flow, and
    (b) a user feedback system,
    said user feedback system comprising:
        (i) a sensing device capable of generating a sensor signal in response to an actual value of a first inhalation parameter during an inhalation manoeuvre of the user, with the first inhalation parameter being selected from inspiratory flow rate, inspiratory pressure and inhaled volume;
        (ii) an electronic memory capable of storing one or more target ranges for the first inhalation parameter;
        (iii) a signalling device comprising a first signalling member capable of emitting light of varying intensity; and
        (iv) a controller capable of receiving the sensor signal generated by the sensing device, reading the electronic memory, and controlling the signalling device based on the sensor signal;
    wherein the user feedback system is configured to indicate to the user during the inhalation manoeuvre whether the actual value of the first inhalation parameter is within a first target range by means of proportionately varying the intensity of the light emitted by the first signalling member based on the extent of deviation of the actual value from the first target range.

2. The inhalation device of claim 1, wherein the flow restrictor is responsive to the inspiratory pressure.

3. The inhalation device of claim 1, further comprising a timer capable of generating a time signal, wherein the controller is capable of receiving said time signal, and wherein the feedback system is configured to indicate to the user during an inhalation manoeuvre by means of an output signal that a predetermined period of time has elapsed.

4. The inhalation device of claim 1, wherein said inhalation device further comprises a shut-off feature to interrupt the air flow wherein the shut-off feature is controlled by the controller in response to a sensor signal received from the sensing device and/or to a time signal received from a timer.

5. The inhalation device of claim 1, wherein the sensing device comprises at least one selected from the group consisting of a pressure sensor, a flow sensor, a velocity sensor, a temperature sensor, a microphone, and any combination thereof.

6. The inhalation device of claim 1, wherein the first signalling member is a light emitting diode or a laser diode.

7. The inhalation device of claim 1, wherein the first signalling member is not directly visible by the user, but arranged such that the user receives diffused light.

8. The inhalation device of claim 1, further comprising a mouthpiece, wherein said mouthpiece is illuminated by the light from the first signaling member, and wherein at least a part of the mouthpiece is made from a translucent material.

9. The inhalation device of claim 1, wherein the device is hand-held.

10. An inhalation device for enabling a user to inhale at a desired inspiratory flow rate and/or inspiratory pressure, comprising
- (a) a flow restrictor to restrict the air flow, and
- (b) a user feedback system, said user feedback system comprising:
- (i) a sensing device capable of generating a sensor signal in response to an actual value of a first inhalation parameter during an inhalation manoeuvre of the user, with the first inhalation parameter being selected from inspiratory flow rate, inspiratory pressure and inhaled volume;
- (ii) an electronic memory capable of storing one or more target ranges for the first inhalation parameter;
- (iii) a mouthpiece capable of emitting light; and
- (iv) a controller capable of receiving the sensor signal generated by the sensing device, reading the electronic memory, and controlling the mouthpiece;

wherein the user feedback system is configured to indicate to the user during the inhalation manoeuvre by means of the light emitted by the mouthpiece whether the actual value of the first inhalation parameter is within a first target range by means of varying the intensity of the light emitted by the mouthpiece based on the extent of deviation of the actual value from the first target range.

11. The inhalation device of claim 10, wherein at least a part of the mouthpiece is made from a translucent material.

12. The inhalation device of claim 1, wherein the light emitted by the first signaling member decreases in intensity the further the actual value of the first inhalation parameter deviates from the first target range, and wherein the decrease in intensity is proportional to the extent of deviation of the actual value of the first inhalation parameter from the first target range.

* * * * *